(12) United States Patent
Zhang

(10) Patent No.: US 6,646,131 B2
(45) Date of Patent: Nov. 11, 2003

US006646131B2

(54) RESOLUTION OF THE ENANTIOMERS OF AMLODIPINE

(76) Inventor: Xitian Zhang, N. 159 Remin Street, Changchun, JiLin (CN), 130022

( * ) Notice: Subject to any disclaimer, the term of this patent is extended or adjusted under 35 U.S.C. 154(b) by 0 days.

(21) Appl. No.: 10/203,615

(22) PCT Filed: Dec. 8, 2000

(86) PCT No.: PCT/CN00/00538

§ 371 (c)(1),
(2), (4) Date: Aug. 16, 2002

(87) PCT Pub. No.: WO01/60799

PCT Pub. Date: Aug. 23, 2001

(65) Prior Publication Data

US 2003/0028031 A1 Feb. 6, 2003

(30) Foreign Application Priority Data

Feb. 21, 2000 (CN) ........................ 00102701 A

(51) Int. Cl.[7] .......................................... C07D 213/803
(52) U.S. Cl. ...................................................... 546/321
(58) Field of Search ........................................ 546/321

(56) References Cited

U.S. PATENT DOCUMENTS 5,750,707 A * 5/1998 Spargo ........................ 546/321
6,046,338 A * 4/2000 Spargo ........................ 546/322

FOREIGN PATENT DOCUMENTS

| CN | 1144523 A | 3/1995 |
|---|---|---|
| EP | 0331315 A2 | 9/1989 |
| WO | WO95/25722 | 9/1995 |

OTHER PUBLICATIONS

Goldman et al, Angew. Chemie, Int. Ed. Engl, vol. 301, 1991. pp. 1559–1578, 1,4–Dihydropyridines: Effects of Chirality . . . .

* cited by examiner

Primary Examiner—Patricia L. Morris
(74) Attorney, Agent, or Firm—Jacobson Holman PLLC

(57) ABSTRACT

The invention provides a feasible method for the separation of both (S)-(−)-enantiomer and (R)-(+)-enantiomer of racemic amlodipine with higher optically purity. The chiral reagent for separation is tartaric acid and the chiral auxiliary reagent is hexadeuterium dimethyl sulphoxide (DMSO-$d_6$).

4 Claims, No Drawings

RESOLUTION OF THE ENANTIOMERS OF AMLODIPINE

This is a nationalization of PCT/CN00/00538, filed Dec. 8, 2000 and published in Chinese.

TECHNICAL FIELD

The invention provides a feasible method for the separation of both (S)-(−)-enantiomer and (R)-(+)-enantiomer of racemic amlodipine. The chiral reagent for separation is tartaric acid and the chiral auxiliary reagent is hexadeuterium dimethyl sulphoxide (DMSO-$d_6$).

BACKGROUND (S)-(−)-amlodipine and its salts are long-acting calcium channel blockers, and are thus useful for the treatment of hypertension and angina and (R)-(+)-amlodipine also exhibits activity in the treatment or prevention of atherosclerosis.

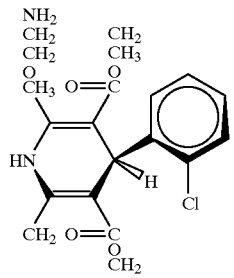

(S)-(−)-amlodipine

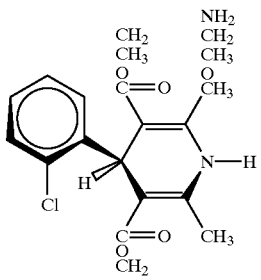

(R)-(+)-amlodipine

Pfizer invented a feasible method for the separation of the enantiomers of amlodipine (W095/25722), in very good optical purity and yield. The use of both dimethyl sulphoxide (DMSO) and chiral reagent tartaric acid are essential to this method.

The invention indicates that hexadeuterium dimethyl sulphoxide (DMSO-$d_6$), in optical purity of up to 100% e.e. and very good yield, is a chiral auxiliary reagent better than DMSO.

CONTENTS OF THE INVENTION

The invention provides a feasible method for the separation of racemic amlodipine. The chiral reagent for separation is L-tartaric acid or D-tartaric acid and the chiral auxiliary reagent is hexadeuterium dimethyl sulphoxide (DMSO-$d_6$), in the amlodipine and tartaric acid mole ratio of about 1:0.25. The resulting precipitate is (S)-(−)-amlodipine-hemi-D-tartrate-mono-DMSO-$d_6$ solvate or (R)-(+)-amlodipine-hemi-L-tartrate-mono-DMSO-$d_6$ solvate.

The separation methods used for precipitate are filtration, centrifugation or decantation.

The above precipitate can further be treated to give (R)-(+)-amlodipine or (S)-(−)-amlodipine.

The mother solution after removal of the above precipitate can be treated with 0.25-mole equivalent of the antipode of tartaric acid (such as originally used L-tartaric acid and now used D-tartaric acid), which results in precipitation of the antipodal amlodipine and tartrate and DMSO-$d_6$ solvate.

The hexadeuterium dimethyl sulphoxide solvents for carrying out the resolution are sulphoxides, ketones, alcohols, ethers, amides, esters, chlorohydro-carbons, water, nitrites and hydrocarbons. The common solvents are DMSO-$d_6$, DMSO, acetone, methylethyl ketone, isopropyl alcohol, diethyl ether, tetrahydrofuran, N,N'-dimethylformamide, N,N-dimethylpropylene-urea, ethyl acetate, chloroform, dichloromethane, 1,2-dichloroethane, 1,1,1-trichloroethane, acetonitrile and toluene.

The maximum amount of some solvent employed is variable. A man skilled in the art will readily be able to establish the appropriate proportion, but DMSO-$d_6$/amlodipine 1 (mole ratio).

Recrystallisation solvents for the tartrate salt are alcohols, such as methanol.

The bases for the preparation of amlodipine from its salts are metal hydroxides, oxides, carbonates and amides. The most convenient is sodium hydroxide.

The crystalline precipitate constituent is (S)-(−)-amlodipine-hemi-tartrate-mono-DMSO-$d_6$ solvate or R-(+)-amlodipine-hemi-tartrate-mono-DMSO-$d_6$ solvate respectively.

IMPLEMENTATION OF THE INVENTION

In the following examples, optical purities were measured by chiral HPLC. The HPLC conditions used for this separation were as follows: chiral column-ultron ES-OVM, Ovomucoid, 15 cm; flow rate, 0.3 ml/min; detection wavelength, 360 nm; mobile phase, disodium hydrogen-phosphate (20 mM, PH 7)/acetonitrile=80/20. Samples were dissolved in acetonitrile/water=50/50, 0.3 mg/ml solution.

EXAMPLE 1

(S)-(−)-amlodipine-hemi-D-tartrate-mono-DMSO-$d_6$ Solvate and (R)-(+)-amlodipine-hemi-L-tartrate-mono-DMSO-$d_6$ Solvate From (R, S)-amlodipine To a stirred solution of 5 g (R, S)-amlodipine in 22.9 g DMSO-$d_6$ was added a solution of 0.458 g D-tartaric acid (0.25 mole equivalents) in 22.9 g DMSO-$d_6$. Precipitation began within one minute, and the resulting slurry was stirred at room temperature overnight. The solid was collected by filtration, washing with 20 ml acetone. It was then dried at 50 in vacuo overnight to give 2.36 g (68% of theoretical yield) (S)-(−)-amlodipine-hemi-D-tartrate-mono-DMSO-$d_6$ solvate, m.p. 158–160 (Found: C 50.81%, H(D) 7.09%, N 4.84%, $C_{20}H_{25}N_2O_5Cl$ 0.5 $C_4H_6O_6$ $C_2D_6OS$; Calc. for C 50.74%, H (D) 7.04%, N 4.90%), optical purity 99.9% d.e. by chiral HPLC.

0.44 g L-tartaric acid (0.25 mole equivalents) was added to the filtered fluid and stirred at room temperature overnight. The solid was collected by filtration, washing with 20 ml acetone. It was then dried at 50 in vacuo overnight to give 2.0 g (55% of theoretical yield) (R)-(+)-amlodipine-hemi-L-tartrate-mono-DMSO-$d_6$ solvate, m.p. 158–160, (Found: C 50.67%, H (D) 6.95%, N 4.90%, $C_{20}H_{25}N_2O_5Cl$ 0.5 $C_4H_6O_6$ $C_2D_6OS$: Calc. for C 50.74%, H (D) 7.04%, N 4.93%), optical purity 99.5% d. e. by chiral HPLC.

EXAMPLE 2

(S)-(−)-amlodipine From (S)-(−)-amlodipine-hemi-D-tartrate-mono-DMSO-$d_6$ Solvate 5 g (S)-(−)-amlodipine-hemi-D-tartrate-mono-DMSO-$d_6$ solvate and 56 ml 2N NaOH water solution were stirred together with 56 ml $CH_2Cl_2$ for 40 minutes. The organic solution was separated off and washed with water. The $CH_2Cl_2$ was distilled off and hexane was added and stirred to crystallize it. The solid was collected by filtration and dried at 50 in vacuo overnight to give 3.20 g (88% of theoretical yield) (S)-(−)-amlodipine, m.p. 107–110, (Found: C 58.69%, H 6.09%, N 6.84%; Calc. for $C_{20}H_{25}N_2O_5Cl$: C 58.75%, H 6.16%, N 6.85%), $[\ ]_D^{25}$ −32.6 (C=1, MeOH), optical purity 99.9% e.e. by chiral HPLC.

EXAMPLE 3

(R)-(+)-amlodipine From (R)-(+)-amlodipine-hemi-L-tartrate-mono-DMSO-$d_6$ Solvate 5 g (R)-(+)-amlodipine-hemi-L-tartrate-mono-DMSO-$d_6$ solvate and 56 ml 2N NaOH water solution were stirred together with 56 ml $CH_2Cl_2$ for 40 minutes. The $CH_2Cl_2$ was distilled off and hexane was added and stirred to crystallize it. The solid was collected by filtration and dried at 50
in vacuo overnight to give 3.31 g (91% of theoretical yield) (R)-(+)-amlodipine, m.p. 107–110, (Found: C 58.41%, H 6.05%, N 6.62%; Calc. for $C_{20}H_{25}N_2O_5Cl$: C 58.75%, H 6.16%, N 6.85%), $[\ ]_D^{25}$ +32.6 (C=1, MeOH), optical purity 99.5% e.e. by chiral HPLC.

EXAMPLE 4

(S)-(−)-amlodipine-hemi-D-tartrate-mono-DMSO-$d_6$ Solvate and R-(+)-amlodipine-hemi-L-tartrate-mono-DMSO-$d_6$ Solvate From (R, S)-amlodipine.

The method of example 1 was used, but substituting the DMSO-$d_6$ with a mixed solvent and DMSO-$d_6$/amlodipine 1 (mole ratio). $V_{solvent}/(V_{DMSO-d6}+V_{solvent})$ was shown in percentages. $(V_{DMSO-d6}+V_{solvent})/M=4\sim18$, in which, V, volume, ml; solvent; M, mass of amlodipine, g. The solvate can then be processed to (S)-(−)-amlodipine and (R)-(+)-amlodipine according to the procedures of examples 2 and 3.

heated to 60 under protection of nitrogen. After dissolution, with stirring stopped, the solution was cooled to room temperature and then crystallized overnight. The solid was collected by filtration, washing with 20 ml water, and then the benzene sulfonic acid (S)-(−)-amlodipine was dried at 50 in vacuo overnight to give 6.2 g (90% of theoretical yield), (Found: C 54.85%, H 5.15%, N 5.58%; Calc. for $C_{20}H_{25}N_2O_5Cl$: C 54.72%, H 5.14%, N 5.34%), $[\ ]_D^{25}$ −24.9 (C=1, MeOH), optical purity 99.9% e.e. by chiral HPLC.

INDUSTRIAL APPLICABILITY

The invention provides a feasible method for the separation of racemic amlodipine, which uses hexadeuterium dimethyl sulphoxide as the chiral auxiliary reagent to separate the enantiomers of racemic amlodipine with a time separation in optical purities of up to 100% e.e. and in yield of up to 68%, this high pure (S)-(−)-amlodipine is higher security for patients. Hexadeuterium dimethyl sulphoxide is reclaimed without notable cost augment for its wastage, so susceptible of industrial application.

What is claimed is:

1. A method for the separation of (R)-(+)- and (S)-(−)-isomers of amlodipine from mixtures thereof, which comprises the reaction of the mixture of isomers with D- or L-tartaric acid as a chiral reagent, wherein the mole ratio of tartaric acid to amlodipine is 0.25, in a) hexadeuterium dimethyl sulphoxide (DMSO-$d_6$) or b) an organic solvent containing DMSO-$d_6$ for precipitation of, respectively, a DMSO-$d_6$ solvate of D-tartrate salt of (S)-(−)-amlodipine, or a DMSO-$d_6$ solvate of a L-tartrate salt of (R)-(+)-amlodipine.

2. A method according to claim 1, wherein the reaction is effected in an organic solvent containing DMSO-$d_6$.

3. The method according to claim 2, wherein the organic solvent is a member selected from the group consisting of water, sulphoxide, ketone, alcohol, ether, amide, ester, chloride, nitrile or hydrocarbon, wherein precipitation of the DMSO-$d_6$ solvate takes place.

TABLE

| Solvent | solvent %* | (S)-(−)-enantiomer % e.e.* | (R)-(+)-enantiomer % e.e.* |
|---|---|---|---|
| methylethyl ketone | 2 | 99.0 | 98.7 |
| toluene | 2 | 92.0 | 91.7 |
| Isopropyl alcohol | 5 | 92.6 | 92.4 |
| $H_2O$ | 10 | 98.5 | 98.4 |
| dimethyl acetamide | 10 | 98.3 | 98.1 |
| tetrahydrofuran | 33 | 98.6 | 98.5 |
| ethyl acetate | 50 | 99.2 | 99.1 |
| dichloromethane | 50 | 100 | 99.8 |
| diethyl sulphoxide | 50 | 98.1 | 98.4 |
| diethyl sulphoxide | 72 | 91.1 | 90.5 |
| dimethyl sulphoxide | 90 | 94.5 | 94.1 |
| acetone | 50 | 99.2 | 99.0 |
| acetone | 70 | 95.7 | 96.1 |
| acetone | 90 | 95.4 | 95.7 |
| acetone | 97 | 96.8 | 96.5 |
| acetone | 99 | 95.4 | 95.1 |

*Measured by chiral HPLC.

EXAMPLE 5

Benzene Sulfonic Acid (S)-(−)-amlodipine 5 g (S)-(−)-amlodipine was put into 120 ml water and 1.4 g benzene sulfonic acid was added and stirred, which was 4. The method according to claim 2, wherein the solvate precipitated is, respectively, (S)-(−)-amlodipine-hemp-D-tartrate-mono-DMSO-$d_6$-solvate or (R)-(+)-amlodipine-hemi-L-tartrate-mono-DSMO-$d_6$-solvate.

* * * * *